United States Patent [19]

Brown

[11] 4,137,495
[45] Jan. 30, 1979

[54] OIL DETECTOR

[76] Inventor: David M. B. Brown, 1 Milton Park, Colyton, Ayr, Ayrshire, Scotland

[21] Appl. No.: 781,352

[22] Filed: Mar. 25, 1977

[30] Foreign Application Priority Data

Mar. 27, 1976 [GB] United Kingdom ............... 39885/76

[51] Int. Cl.² .......................................... G01N 27/42
[52] U.S. Cl. ................................. 324/30 B; 324/65 R
[58] Field of Search .................... 324/29, 30 R, 30 B, 324/65 R; 340/236; 204/195 R

[56] References Cited

U.S. PATENT DOCUMENTS

| 2,082,213 | 6/1937 | O'Donnell | 324/30 B |
| 3,234,117 | 2/1966 | Rost et al. | 204/195 R |
| 3,265,962 | 8/1966 | Otto, Jr. | 324/30 B |
| 3,523,070 | 8/1970 | Silverman et al. | 204/195 R |
| 3,781,660 | 12/1973 | Ludt | 324/30 B |
| 3,800,219 | 3/1974 | Fosberg | 340/236 |
| 3,916,674 | 11/1975 | Miller | 340/236 |

Primary Examiner—M. Tokar

[57] ABSTRACT

This invention is concerned with an oil detector comprising a pair of electrodes having therebetween a capillary channel of such a size that water and oil will be held therein by surface tension, and means for electrically connecting the electrodes to a measuring circuit.

9 Claims, 6 Drawing Figures

OIL DETECTOR

This invention relates to an oil detector.

In situations where large quantities of oil are being handled near water (for example, at tanker terminals), it is important that any oil leaks or spillages are detected as quickly as possible in order that they may be dealt with before they can cause serious environmental damage. In daylight, any oil on water is easily detected visually but tanker terminals normally operate throughout the day and night and the detection of leaks or spillages during darkness presents considerable problems. Indeed, there have been incidents in which large quantities of oil have escaped during darkness without being detected.

The present invention provides a detector which can indicate the presence of oil on water.

Accordingly, the invention provides an oil detector comprising a pair of electrodes having therebetween a capillary channel of such a size that water and oil will be held therein by surface tension, and means for electrically connecting the electrodes to a measuring circuit.

The electrodes in the device of this invention are preferably liquid electrodes comprising either a mass of porous material (which may be a non-conductor, such as blotting paper) which in use is impregnated with an electrolyte to provide the necessary conductivity, or chambers which may be filled with an electrolyte. Alternatively, the "electrodes" may simply take the form of chambers which will be filled with water when the detector is in use.

In use, the detector of the invention is connected to a measuring circuit capable of responding to changes in the electrical resistance between the electrodes. When the detector is then placed, immersed in but adjacent the surface of, water free from oil, the channel becomes filled with water and current can flow between the electrodes. If, however, there is oil floating on the water, it is oil which enters the channel, thereby greatly raising the electrical resistance between the electrodes. The change in the resistance between the electrodes is detected by a measuring circuit and used to activate a warning system. It has been found that appropriate adjustment of the size of the capillary channel will enable the detector to signal the presence of small quantities of oil but not to be affected by the surface film which is almost always present near to moored ships or in harbours.

To facilitate the entry of the very viscous oil into the capillary channel, it is desirable that a small bore be provided intersecting the channel and through which, when the detector is immersed in water, water can enter or leave the channel.

Preferred embodiments of the invention will now be described, though by way of illustration only, with reference to the accompanying drawings, in which.

Figure 1:
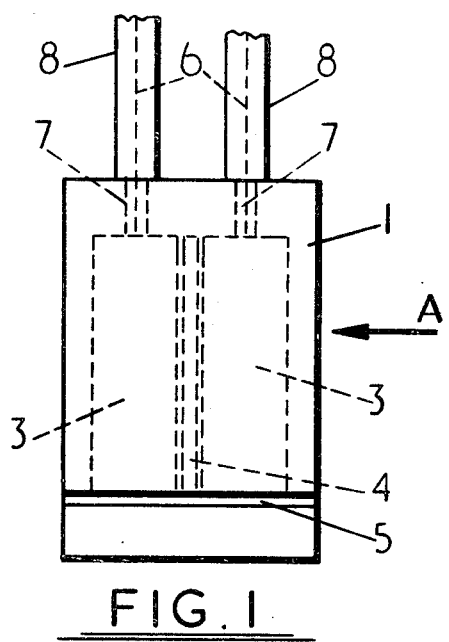
FIG. 1 is a plan view of a first oil detector of the invention.
Figure 2:
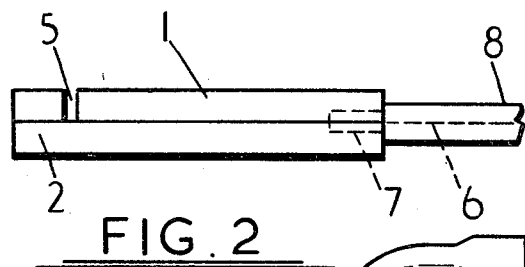
FIG. 2 is a side view looking in the direction of arrow A in FIG. 1.

The oil detector shown in FIGS. 1 and 2 comprises two parallel synthetic resin plates 1 and 2 between which are sandwiched two electrodes 3. Those electrodes are made of blotting paper which, although effectively nonconductive when dry, becomes conductive when it is saturated with water. To prevent short circuits between the electrodes 3, they are separated by a synthetic resin divider 4.

At the lower end of the detector (as seen in FIG. 1) a channel 5 is cut through the plate 1 so exposing the ends of the electrodes 3. The channel 5 is sufficiently narrow for water or oil to be held therein by surface tension.

At the opposed end of the electrodes 3, wires 6 run from the electrodes through apertures 7 in the plates 1 and 2 to a measuring circuit (not shown). Beyond the apertures 7, the wires 6 are enclosed within flexible rubber tubes 8, the annular spaces between the wires and the tubes being filled with tap water, which is provided for two reasons. Firstly, this tap water keeps the electrodes saturated with water of constant composition and thus avoids unnecessary changes in resistance which might disturb the measuring circuit. Secondly, if the detector is momentarily lifted out of the water by wave action, the tap water keeps the channel 5 filled with water, thus preventing the spurious signals which would be derived from the detector if the channel became filled with air.

In use, the detector shown in the figures is mounted, channel end downwards, on a small float so that it lies adjacent the water surface, the small float being attached by means of a flexible connector to a conventional buoy. As the float moves vertically with passing waves (a very small wave-height will suffice), the detector is moved in and out of the water and comes into contact with any oil which lies on the surface thereof. It has been found that under these condition, if even a small amount of oil is present on the surface, the oil will quickly replace the water in the channel, thereby greatly increasing the electrical resistance between the electrodes and causing the measuring circuit to give a warning signal, which may be in any convenient form such as a bell, a buzzer or a lamp.

Figure 3:
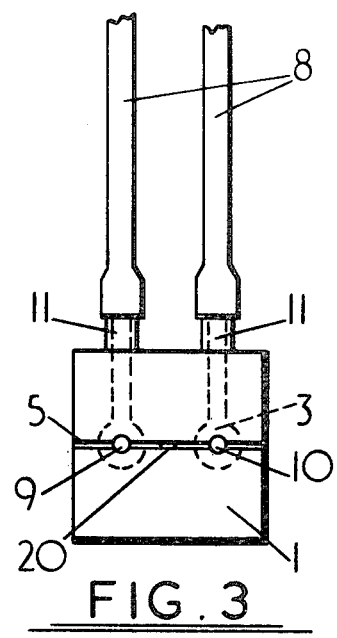
FIG. 3 is a plan view of a second oil detector of the invention.
Figure 4:
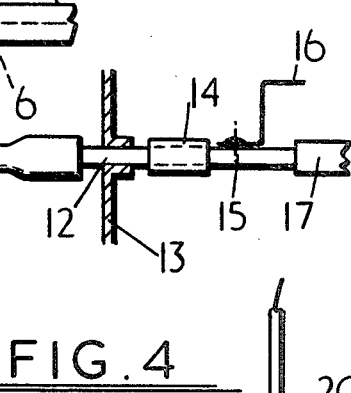
FIG. 4 is an enlarged side elevation, partly in section, of the oil detector shown in FIG. 3.

The oil detector shown in FIGS. 3 and 4 also has electrodes 3 in the form of pads of compressed blotting paper, these pads being thicker and smaller in cross-section than those in the first oil detector described above. A capillary channel 5 is formed in the synthetic resin body 1 of the detector and runs alongside the electrodes 3 communicating with the electrodes via two capillary bores 9 and 10. Between the bores 9 and 10 is located a bore 20 which extends through the body 1, and through which water can enter the channel 5. In this embodiment, in order to avoid the problems associated with connecting wires directly to the electrodes (due to the constant movement of the detector caused by wave action, the wires tend to suffer metal fatigue and may eventually break), electrical connections to the electrodes are established by means of columns of electrolyte 11 confined within bores 7 in the body 1 and within heavy-walled synthetic rubber tubes 8 which extend to the outer ends of hollow tubes 12 of insulating material fixed in one wall 13 of the buoy to which the detector is attached (see FIG. 4). At the opposed ends of the tubes 12, further short lengths 14 of the same heavy-walled rubber tubing connect the tubes 12 to tubular metal connectors 15, to which are attached wires 16 leading to a resistance measuring circuit. Electrolyte is fed to the connectors 15 via rubber tubes 17 either by gravity or under pressure so that there is a slow flow of electrolyte through the electrodes 3.

Figure 6:
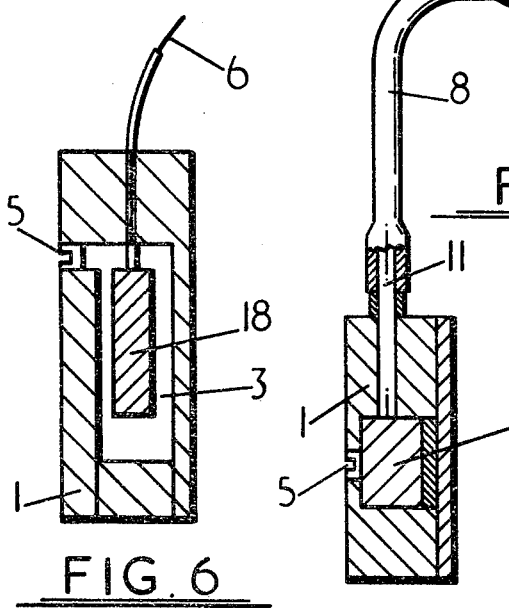
FIG. 6 is an enlarged section along the line VI—VI in FIG. 5.
Figure 5:
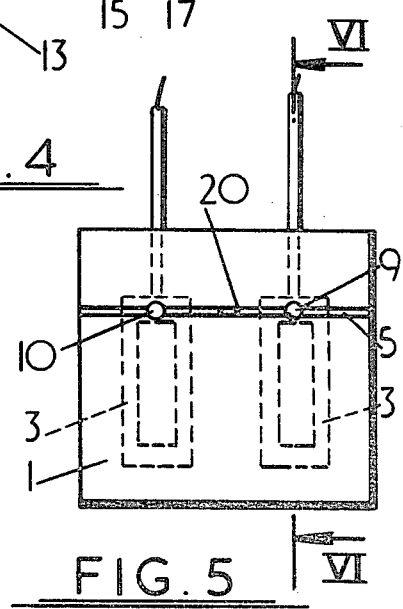
FIG. 5 is a plan view of a third oil detector of the invention.

The third oil detector of the invention shown in FIGS. 5 and 6 has "electrodes" in the form of chambers 3 which communicate via capillary bores 9 and 10 with a capillary channel 5 formed in the synthetic resin body 1 of the detector. Before the detector is immersed in water, the chambers 3 are filled with water through the bores 9 and 10. An aperture 20 is again provided between the bores 9 and 10 to assist the entry of water into the channel 5.

To establish electrical connections with the chambers 3, insulated wires 6 pass through the body 1 of the detector and terminate in metal electrodes 18 lying within the chambers 3.

It will be appreciated that, when this detector is used in salt water, an alternating voltage must be applied to the electrodes to prevent the generation of chlorine gas.

It may be convenient to mount a number of oil detectors of the invention upon a series of floats which are connected together by wires, ropes of the like and placed around an area where oil leaks or spills are likely to occur. Alternatively, the detectors may be mounted upon buoys or other floating structures in areas where such leaks or spills may be expected, or on small floats flexibly attached to such buoys or structures.

What I claim is:

1. An oil detector for detecting the presence of oil floating on a body of water comprising a pair of electrodes, a body member formed of an electrically non-conductive material having a capillary channel therein extending at least between said electrodes and communicating therewith, a bore formed in said body member extending therethrough and intersecting said channel to facilitate the entry of water into said channel when the detector is immersed in water, and means for electrically connecting said electrodes to a measuring circuit, said capillary channel being on an external face of said body member and being exposed to the body of water and being open to receive a water-oil mixture.

2. An oil detector as claimed in claim 1, in which the electrodes are liquid electrodes comprising a mass of porous material capable of being impregnated with an electrolyte.

3. An oil detector as claimed in claim 2, in which the porous material is blotting paper.

4. An oil detector according to claim 1, wherein said electrodes are liquid electrodes each comprising a chamber capable of being filled with an electrolyte.

5. An oil detector as claimed in claim 4, in which the chambers have metal electrodes fixed therein.

6. An oil detector as claimed in claim 2, which further comprises means for supplying electrolyte to the porous material.

7. An oil detector as claimed in claim 6, in which the means for supplying electrolyte to the porous material comprises flexible tubes and columns of electroyte confined within said tubes, said columns of electrolyte also serving as the means for electrically connecting the electrodes to a measuring circuit.

8. An oil detector as claimed in claim 1, further comprising a measuring circuit capable of measuring the resistance between the electrodes and a signalling device capable of emitting a signal when the resistance exceeds a predetermined value.

9. An oil detector according to claim 1, wherein said capillary channel abuts and communicates with said electrodes by means of a pair of capillary bores, each of said bores being open to said channel and said electrodes respectively.

* * * * *